US009339356B2

(12) United States Patent
Gottlieb

(10) Patent No.: US 9,339,356 B2
(45) Date of Patent: May 17, 2016

(54) ELECTRIC INTERDENTAL CLEANING APPARATUS AND SYSTEMS USEFUL FOR CLEANING TEETH AND INTERDENTAL SPACES

(71) Applicant: STEVI LLC, Silver Spring, MD (US)

(72) Inventor: Ray M. Gottlieb, Silver Spring, MD (US)

(73) Assignee: STEVI LLC, Silver Spring, MD (US)

( * ) Notice: Subject to any disclaimer, the term of this patent is extended or adjusted under 35 U.S.C. 154(b) by 0 days.

(21) Appl. No.: 14/552,434

(22) Filed: Nov. 24, 2014

(65) Prior Publication Data

US 2015/0216639 A1 Aug. 6, 2015

Related U.S. Application Data

(60) Provisional application No. 61/935,830, filed on Feb. 4, 2014.

(51) Int. Cl.
| | | |
|---|---|---|
| *A61C 15/00* | (2006.01) | |
| *A61C 17/26* | (2006.01) | |
| *A61C 17/22* | (2006.01) | |
| *A61C 17/34* | (2006.01) | |

(52) U.S. Cl.
CPC ............... *A61C 15/00* (2013.01); *A61C 17/222* (2013.01); *A61C 17/26* (2013.01); *A61C 17/3463* (2013.01)

(58) Field of Classification Search
CPC ...... A61C 15/00; A61C 17/222; A61C 17/26; A61C 17/3463
See application file for complete search history.

(56) References Cited

U.S. PATENT DOCUMENTS

| | | | |
|---|---|---|---|
| 4,603,448 | A | 8/1986 | Middleton et al. |
| 5,071,348 | A | 12/1991 | Woog |
| 5,145,369 | A | 9/1992 | Lustig et al. |
| 5,499,420 | A | 3/1996 | Boland |
| 5,535,474 | A | 7/1996 | Salazar |
| 5,623,746 | A | 4/1997 | Ichiro |
| 5,647,385 | A | 7/1997 | Zebuhr |
| 5,732,433 | A | 3/1998 | Göcking et al. |
| 5,850,655 | A | 12/1998 | Göcking et al. |
| 6,106,290 | A | 8/2000 | Weissman |
| 6,178,579 | B1 | 1/2001 | Blaustein |
| 6,230,354 | B1 | 5/2001 | Sproat |
| 6,237,178 | B1 | 5/2001 | Krammer |
| 6,546,586 | B2 | 4/2003 | Cho |
| 6,574,820 | B1 | 6/2003 | DePuydt et al. |

(Continued)

FOREIGN PATENT DOCUMENTS

EP 1494610 B1 12/2007

OTHER PUBLICATIONS

PCT/US2014/057928, Jan. 5, 2015, International Search Report and Written Opinion of International Searching Authority.

(Continued)

*Primary Examiner* — Shay Karls
(74) *Attorney, Agent, or Firm* — Ditthavong & Steiner, P.C.; Richard A. Castellano

(57) ABSTRACT

A powered dental and interdental cleaning tool includes a body, an interdental cleaning member, and a drive member. The drive member extends from the body at an angle to a longitudinal axis of the body. The drive member is connected to the interdental cleaning member. A neck extends from the body and defines a drive member shaft for containing and supporting the drive member.

21 Claims, 5 Drawing Sheets

(56) References Cited

U.S. PATENT DOCUMENTS

| | | |
|---|---|---|
| 6,735,804 B2 | 5/2004 | Carlucci |
| 6,760,946 B2 | 7/2004 | DePuydt |
| 7,150,061 B2 | 12/2006 | Kwong |
| 7,311,108 B2 | 12/2007 | Getgey et al. |
| 7,421,753 B2 | 9/2008 | Chan |
| 7,448,107 B2 | 11/2008 | DePuydt |
| 7,832,042 B2 | 11/2010 | DePuydt |
| 7,941,886 B2 | 5/2011 | Chenvainu et al. |
| 8,011,057 B2 | 9/2011 | Nejat |
| 8,220,097 B2 | 7/2012 | DePuydt et al. |
| 8,539,630 B2 | 9/2013 | Gatzemeyer |
| 8,590,546 B2 | 11/2013 | Pruett |
| 2001/0004781 A1 | 6/2001 | Blaustein et al. |
| 2002/0059685 A1 | 5/2002 | Paffrath |
| 2004/0123409 A1 | 7/2004 | Dickie |
| 2005/0102776 A1 | 5/2005 | Mathur |
| 2005/0268409 A1 | 12/2005 | Blaustein et al. |
| 2007/0294847 A1 | 12/2007 | Wang |
| 2009/0029323 A1 | 1/2009 | Nejat |

OTHER PUBLICATIONS

International Preliminary Report on Patentability for International Application No. PCT/US2014/067193, mailed Apr. 14, 2015, 4 pages.
Notification of Transmittal of Translation of the International Preliminary Report on Patentability (Chapter I or Chapter II) along with Written Opinion of the International Searching Authority for International Application No. PCT/US2014/067193, mailed Apr. 14, 2015, 8 pages.
Non-Final Office Action for U.S. Appl. No. 14/499,163, mailed Jan. 6, 2016, 34 pages.
Notification of Transmittal of and International Preliminary Report on Patentability for International Application No. PCT/US2014/067193, mailed Jan. 19, 2016, 8 pages.
Notification of Transmittal of and International Preliminary Report on Patentability for International Application No. PCT/US2014/057928, mailed Jan. 19, 2016, 11 pages.
US 6,598,254, 07/2003, Blaustein et al. (withdrawn)

ELECTRIC INTERDENTAL CLEANING APPARATUS AND SYSTEMS USEFUL FOR CLEANING TEETH AND INTERDENTAL SPACES

CROSS-REFERENCE TO RELATED APPLICATION

This application claims the benefit of priority to U.S. Provisional Patent Application No. 61/935,830, titled MULTI-FUNCTION ELECTRIC BRUSH APPARATUS AND SYSTEMS USEFUL FOR CLEANING TEETH AND INTERDENTAL SPACES, filed Feb. 4, 2014, the disclosure of which is hereby incorporated by reference herein in its entirety.

FIELD

The disclosure generally relates to oral hygiene tools. In particular, the disclosure relates to electric cleaning tools having a brush for cleaning teeth and interdental spaces.

BACKGROUND

A toothbrush is an oral hygiene instrument that is useful for cleaning teeth and gums. Conventional toothbrushes may include one or more heads of bristles that are arranged for cleaning the oral cavity—particularly, the teeth, tongue, and gums. Toothpaste is typically an abrasive fluid, paste, or gel dentifrice, and is used with toothbrushes to enhance cleaning by mechanical action. The cleaning effectiveness of toothbrushes has also been enhanced by using different bristle textures, sizes, and forms. In the past century, conventional toothbrushes have been modified to include soft bristles to protect tooth enamel and minimize gum damage or irritation, and may be formed of nylon or other materials that have desirable hardness and durability.

Some conventional toothbrushes are powered by electricity. An electric toothbrush includes a brush that is driven by a motor that oscillates or rotates the brush. Electric toothbrushes have been found to be easier to use than brushes that require completely manual brushing action. Moreover, electric toothbrushes have been clinically proven to generally be more effective for cleaning teeth than unpowered toothbrushes.

Other types of conventional toothbrushes include interdental or interproximal brushes and end-tufted brushes. Interdental cleaning instruments such as interdental brushes are designed for cleaning between teeth, and between braces and teeth. An interdental cleaning instrument may have a cleaning head that has a tapered surface profile. For example, a head of an interdental cleaning instrument may have a conical shape for cleaning the narrow spaces between teeth. An interdental cleaning instrument may alternatively include a brush having bristles located about a slender rod that is suitable for sliding between teeth to clean interdental spaces.

End-tufted toothbrushes are designed for cleaning along gumlines adjacent to teeth. End-tufted toothbrushes typically include a bristle head that is shaped to form an angled cleaning surface that conforms to interdental spaces.

SUMMARY

A need has been recognized for an electric interdental cleaning device configured for easier, more effective, and more comprehensive interdental space cleaning. Embodiments of the invention may provide solutions to this and other problems and needs in the art that have not yet been fully identified, appreciated, or solved by current dental cleaning technologies.

A powered interdental cleaning device of embodiments advantageously enables cleaning of tooth surfaces and interdental spaces by way of a rotating and pulsing interdental cleaning member. The interdental cleaning device may be useful for orthodontic, pedodontal, and periodontal applications, and may enable enhanced subgingival cleaning.

In an embodiment, a powered interdental cleaning apparatus includes a body having a first end and a second end. The apparatus has an interdental cleaning member at a head, a drive member, and a neck. The drive member extends from the first end of the body at an angle to a longitudinal axis of the body. The drive member is connected to the interdental cleaning member. The neck has a first end and a second end, and the neck extends from the first end of the body at the first end of the neck. The neck is configured to define or contain a drive member shaft that contains the drive member.

In an embodiment, the head may include a brush assembly having an interdental cleaning member and a brush support. The brush support may extend from the head to form a cone shape defining a hollow interior. The interdental cleaning member may be slidably positioned and configured to extend through a portion of the hollow interior of the brush support.

The interdental cleaning member may be configured and arranged to enable the interdental cleaning member to pulse or reciprocate axially through an opening at the end of the brush support. The apparatus further includes a drive assembly configured to rotate and cause pulsing movement of the interdental cleaning member.

BRIEF DESCRIPTION OF THE DRAWINGS

In order that the advantages of embodiments of the invention will be readily understood, a more particular description of the disclosure briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

DETAILED DESCRIPTION

Some embodiments of the present invention pertain to a powered interdental cleaning device that enables cleaning of interdental spaces. The interdental cleaning device may be useful for orthodontic, pedodontal, and periodontal applications, and may enable enhanced subgingival cleaning under the gumline. For example, an interdental cleaning member may be configured to reach approximately 3 to 5 millimeters below the gumline, and preferably is configured for cleaning at about 5 millimeters below the gumline. The interdental cleaning member may reach further, however, as a matter of design choice.

Figure 1:
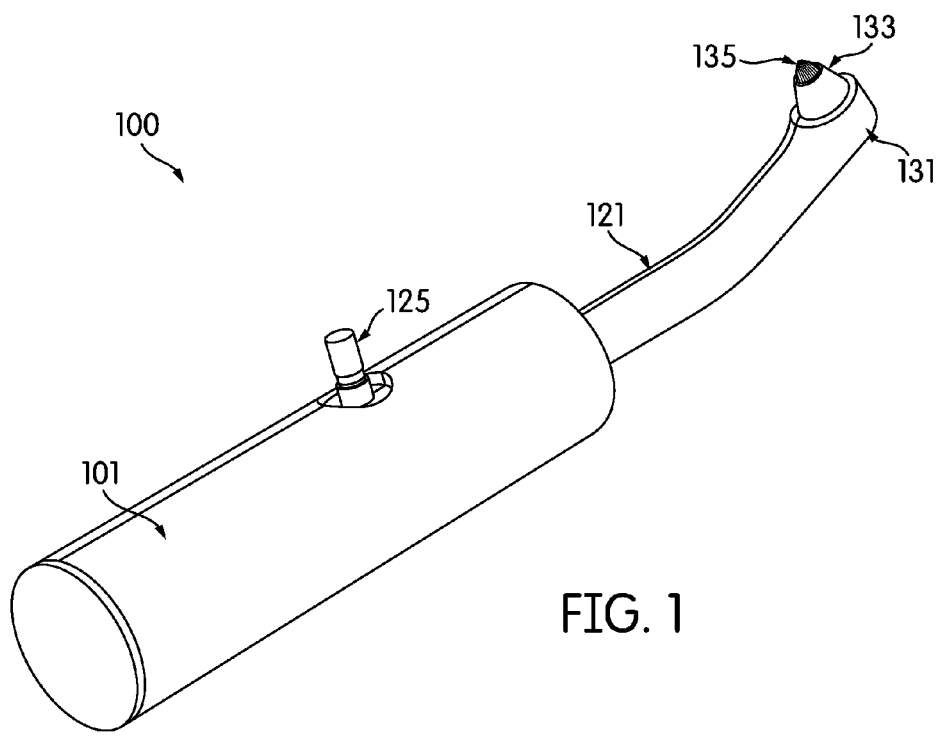
FIG. 1 is a perspective view of an electric interdental cleaning apparatus in accordance with an embodiment.

FIG. 1 is a perspective view of a powered interdental cleaning device 100, according to an embodiment. Interdental cleaning device 100 includes a body 101. Body 101 contains or supports a drive system (not shown).

Body 101 is connected to a neck 121 at a first end of neck 121. A brush assembly head 131 may extend from or be connected to a second end of neck 121. Body 101 may define an opening for access to the drive system. A button, switch, or other now known or later developed actuating mechanism 125 may be connected to the drive system and accessible through the opening of body 101. Actuating mechanism 125 may be configured to enable and cause an adjustment of the drive system. For example, actuating mechanism 125 may facilitate turning on and off the device, and adjusting a speed of the drive system of interdental cleaning device 100. In some embodiments, the drive system may be connected to a variable speed motor (not shown). The motor and actuating mechanism 125 may be configured for variable speed adjustment of the motor, and thus variable speed adjustment of the drive system.

Drive member 107 may be flexible to accommodate angled extension from body 101 to a brush assembly 131. In an embodiment, the angle may be about 20 degrees. In an embodiment, body 101 and neck 121 may have a unitary construction where body 101, neck 121, and brush assembly 131 form a substantially unitary construction. For example, portions of body 101, neck 121, and brush assembly 131 may be formed from a single material.

The brush assembly includes interdental cleaning member 135 and a brush support member 133. Brush support member 133 may be configured to define a central opening, and interdental cleaning member 135 may be disposed for axial and rotational movement inside the substantially cone-shaped support member 133. Electric interdental cleaning device 100 is advantageously suitable for cleaning interdental regions and spaces.

Figure 2:
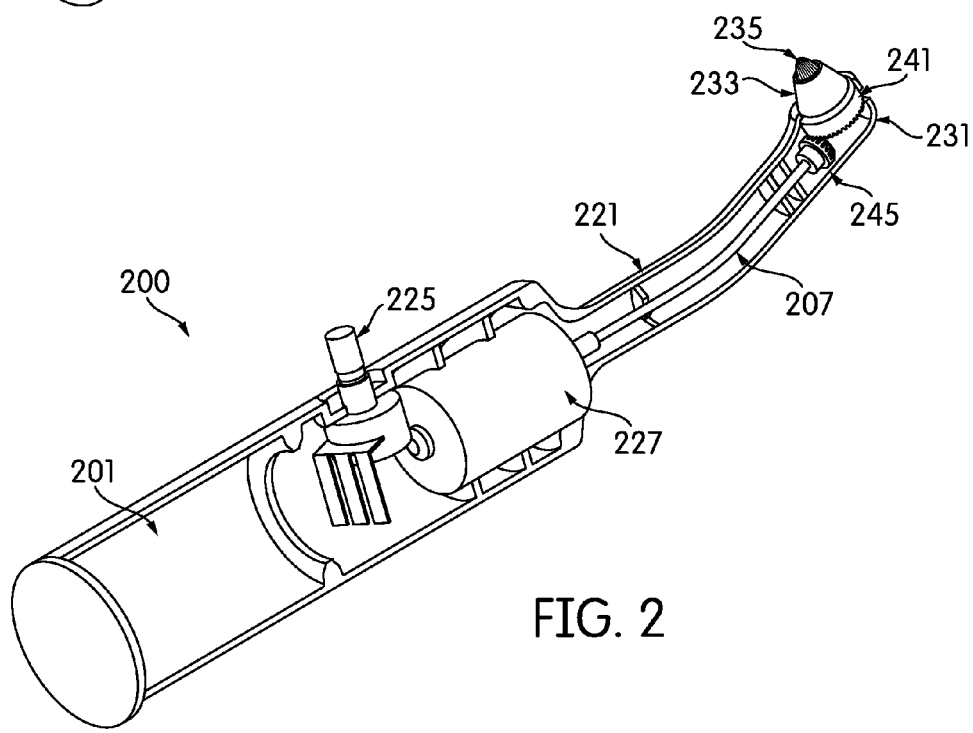
FIG. 2 is a perspective cutaway view of an electric interdental cleaning apparatus showing a drive system in accordance with an embodiment.

FIG. 2 is a perspective view of an electric interdental cleaning device 200 in accordance with an embodiment. Interdental cleaning device 200 has a body 201. Body 201 contains or supports a drive system. The drive system includes a drive member 207. Drive member 207 may be a flexible shaft in some embodiments.

Body 201 is connected to a neck 221 at a first end of neck 221. Neck 221 may include support structures that support drive member 207. Drive member 207 may include a cable, wire, flexible shaft, rod, or any other suitable structure. Drive member 207 may be formed of metal, an alloy, a polymer, a composite, or any other suitable material that is now known or later developed. A head assembly 231 is connected to a second end of neck 221. A button, switch, or other now known or later developed actuating mechanism 225 is connected to the drive system and through an opening of body 201. Actuating mechanism 225 may be configured to enable and cause an adjustment of the drive system. For example, actuating mechanism 225 may facilitate turning interdental cleaning device 200 on and off and adjusting a speed of the drive system. In some embodiments, the drive system may be connected to a variable speed motor (not shown). The variable speed motor and actuating mechanism 225 may be configured for variable speed adjustment of the motor, and thus variable speed adjustment of the drive system.

Drive member 207 is connected to a motor 227 at a first end of drive member 207. Motor 227 may be powered by a power source. The power source may be a battery power source, power from an outlet, or any other suitable AC or DC source, for example. Motor 227 may be connected to actuating mechanism 225 to enable variable speed control. Motor 227 may be anchored for rotation inside body 201.

Drive member 207 may be flexible to accommodate angled extension from body 201 to a brush assembly 231. In some embodiments, the angle may be about 20 degrees. Brush assembly 231 may include an interdental cleaning member 235 and a brush support member 233. Brush support member 233 may be configured to define a central opening, and interdental cleaning member 235 may be disposed for axial and rotational movement inside the opening in a direction substantially perpendicular to a direction of rotation of interdental cleaning member 235.

Drive member 207 may be contained or supported within a drive shaft defined by neck 221. Support structures formed in or defined by the interior of neck 221 may be useful for supporting an angled, flexible drive member. Drive member 207 may be connected at a second end to a crankshaft assembly having a brush assembly support gear 241 and a drive member gear 245. Drive member gear 245 may be attached to and rotated by drive member 207. Drive member gear 245 may be configured to interlock with and cause rotation of brush assembly support gear 241.

The second end of drive member 207 may be attached to an offset connecting rod (not shown). The connecting rod may be associated with a ball and socket assembly (not shown). The ball and socket assembly may connected to interdental cleaning member 235 and may be configured to cause interdental cleaning member 235 to move up and down in a direction perpendicular to the direction of rotation of drive member 207 as drive member 207 rotates.

Brush support member 233 may be connected to brush assembly gear 241. When drive member 207 is rotated by motor 227, drive member gear 245 is caused to rotate brush assembly gear 241 and thus interdental cleaning member 235. Meanwhile, rotating drive member 207 moves the connecting rod to cause pulsing movement of interdental cleaning member 235 through the central opening of brush support member 233. In some embodiments, interdental cleaning member 235 may also be connected to brush assembly gear 241 to enable rotation of interdental cleaning member 235 during the pulsing. For example, when a gear ratio of brush assembly gear 241 and drive member gear 245 is 1:2, interdental cleaning member 235 may pulse in a direction perpendicular to a direction of rotation at a speed of about twice the speed of rotation of interdental cleaning member 235.

Figure 3:
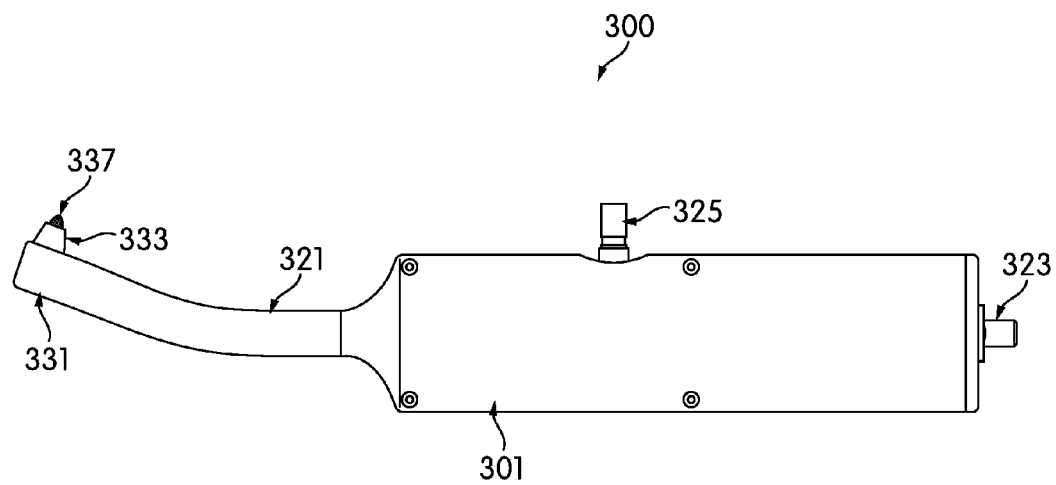
FIG. 3 is a side view of an electric interdental cleaning apparatus in accordance with an embodiment.

FIG. 3 is a side view of an electric interdental cleaning device 300, according to an embodiment. Interdental cleaning device 300 includes a body 301. Body 301 contains or supports a drive system (not shown).

Body 301 is connected to a neck 321 at a first end of neck 321. A head 331 is connected to a second end of neck 321. Body 301 may define an opening for access to the drive system. A button, switch, or other now known or later developed actuating mechanism 325 may be connected to the drive system and accessible through the opening of body 301. Actuating mechanism 325 may be configured to enable and cause an adjustment of the drive system. For example, actuating mechanism 325 may facilitate turning interdental cleaning device 300 on and off and adjusting a speed of the drive system. In some embodiments, the drive system may be connected to a variable speed motor (not shown). The motor and actuating mechanism 325 may be may be configured for variable speed adjustment of the motor, and thus variable speed adjustment of the drive system.

Drive member 307 may be flexible to accommodate angled extension from body 301 to a brush assembly 331. In some embodiments, the angle may be about 20 degrees. Brush assembly 331 may include the interdental cleaning member (not shown) and a brush support member 333. Brush support member 333 may be configured to define a central opening, and the interdental cleaning member 335 may be disposed for axial and rotational movement inside brush support member 335.

Figure 4:
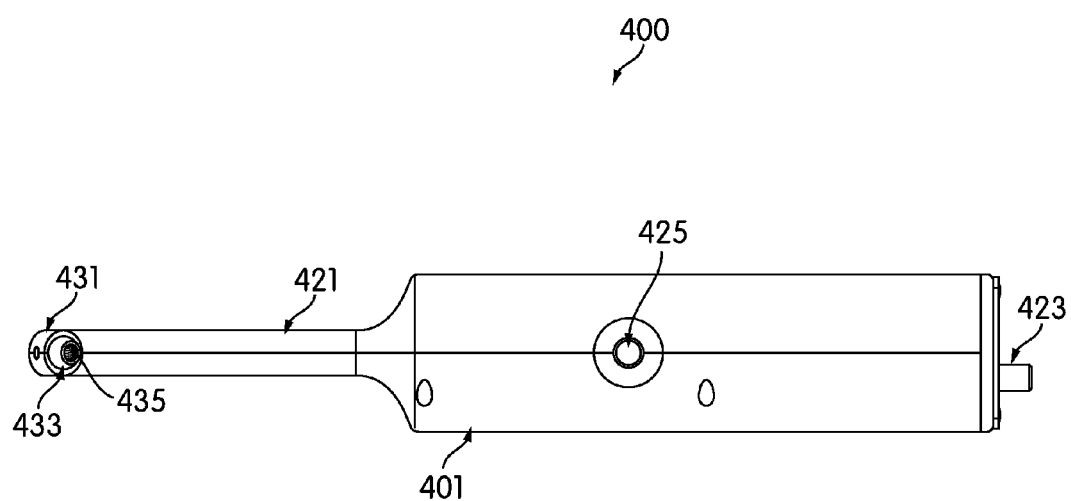
FIG. 4 is a top view of an electric interdental cleaning apparatus in accordance with an embodiment.

FIG. 4 a top view of an interdental cleaning device 400 in accordance with an embodiment. Interdental cleaning device 400 includes a body 401. Body 401 contains or supports a drive system.

Body 401 is connected to a neck 421 at a first end of neck 421. A head 431 is connected to a second end of neck 421. Body 401 may define an opening for access to the drive system. A button, switch, or other now known or later developed actuating mechanism 425 may be connected to the drive system and accessible through the opening of body 401. Actuating mechanism 425 may be configured to enable and cause an adjustment of the drive system. For example, actuating mechanism 425 may facilitate turning apparatus 400 on and off, and adjusting a speed of the drive system.

Drive member 407 may be flexible to accommodate angled extension from body 401 to a brush assembly 431. In some embodiments, the angle may be about 20 degrees. The brush assembly may include an interdental cleaning member 435 and a brush support member 433. Brush support member 433 may be substantially cone-shaped, and may be configured to define a central opening. Interdental cleaning member 435 may be configured and arranged for axial and rotational movement inside the opening.

Figure 5:
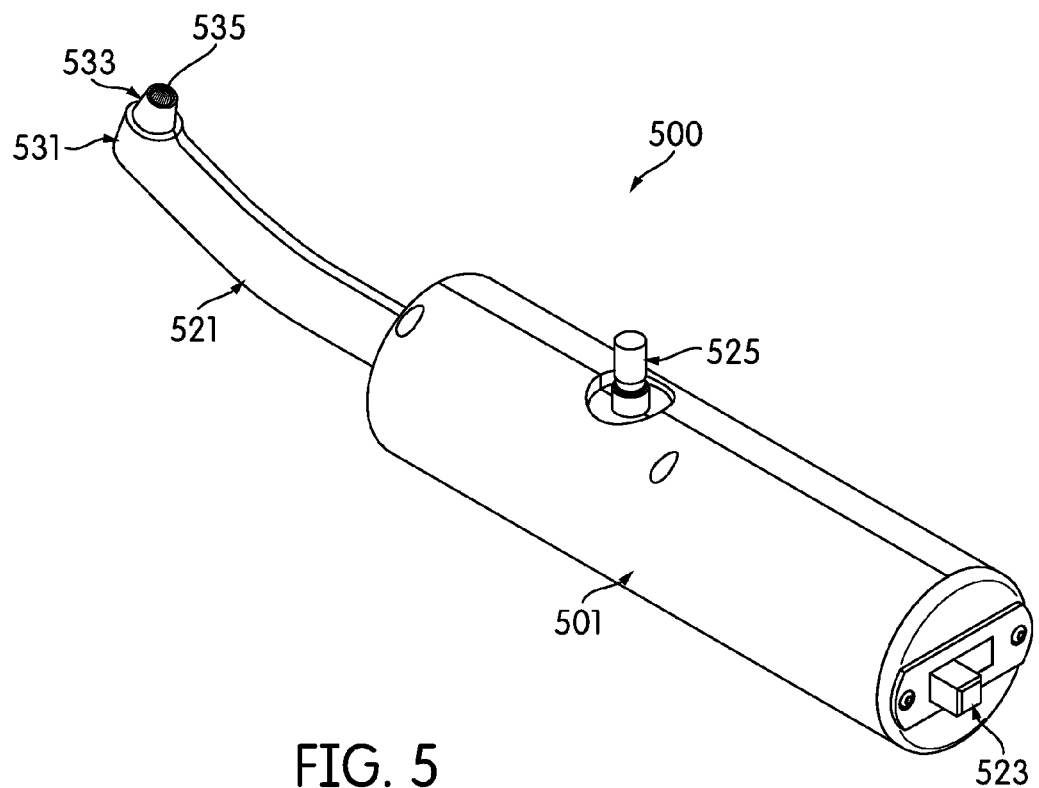
FIG. 5 is a perspective view of an electric interdental cleaning apparatus having a uniform cleaning surface in accordance with an embodiment.

FIG. 5 is a perspective view of an interdental cleaning device 500, according to an embodiment of the present invention. Interdental cleaning device 500 has a body 501. Body 501 contains or supports a drive system (not shown).

Body 501 is connected to a neck 521 at a first end of neck 521. A head 531 is connected to a second end of neck 521. Body 501 may define an opening for access to the drive system. A first button, switch, or other now known or later developed actuating mechanism 523 may be included at an end of body 501, as shown in FIG. 5. Switch 523 may be configured to power a drive system of interdental cleaning device 500 on and off. A second button, switch, or other now known or later developed actuating mechanism 525 may be connected to the drive system and accessible through the opening of body 501. Actuating mechanism 525 may be configured to enable and cause an adjustment of the drive system. For example, actuating mechanism 525 may facilitate turning interdental cleaning device 500 on and off and adjusting a speed of the drive system.

Drive member 507 may be flexible to accommodate angled extension from body 501 to a brush assembly 531. In some embodiments, the angle may be about 20 degrees. The brush assembly may include an interdental cleaning member 535 and a brush support member 533. Brush support member 533 may be configured to define a central opening, and interdental cleaning member 535 may be disposed for axial and rotational movement inside the opening.

Figure 6:
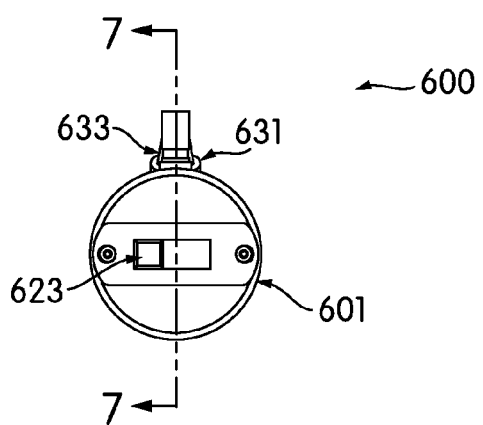
FIG. 6 is an end view of an electric interdental cleaning apparatus in accordance with an embodiment.

FIG. 6 is an end view of an interdental cleaning device 600 in accordance with an embodiment. Interdental cleaning device 600 includes a body 601. Body 601 contains or supports a drive system (not shown).

Body 601 is connected to a neck 621 at a first end of neck 621. A head 631 may be connected to a second end of neck 621. As shown in FIG. 6, body 601 and neck 621 may have a unitary construction where body 601, neck 621, and brush assembly 631 form a substantially unitary construction. For example, portions of body 601, neck 621, and brush assembly 631 may be formed from a single material.

A first button, switch, or other now known or later developed actuating mechanism 623 may be included at an end of body 601 as shown in FIG. 6. Switch 623 may be configured to power a drive system of interdental cleaning device 600 on and off. One or more now known or later developed actuating mechanisms may be connected to the drive system and accessible from an outer portion of body 601, and may be configured to enable and cause an adjustment of the drive system. For example, actuating mechanisms may facilitate turning multi-functional electric brush 600 on and off and adjusting a speed of the drive system. In some embodiments, the drive system may be connected to a variable speed motor. The motor and actuating mechanism may be configured for variable speed adjustment of the motor, and thus variable speed adjustment of the drive system.

The brush assembly may include an interdental cleaning member 635 and a brush support member 633. Brush support member 633 may be configured to define a central opening, and interdental cleaning member 635 may be disposed for axial and rotational movement inside the opening. Brush support member 633 may be fixed, or in alternative embodiments, may be connected to the gear assembly for rotation.

Figure 7:
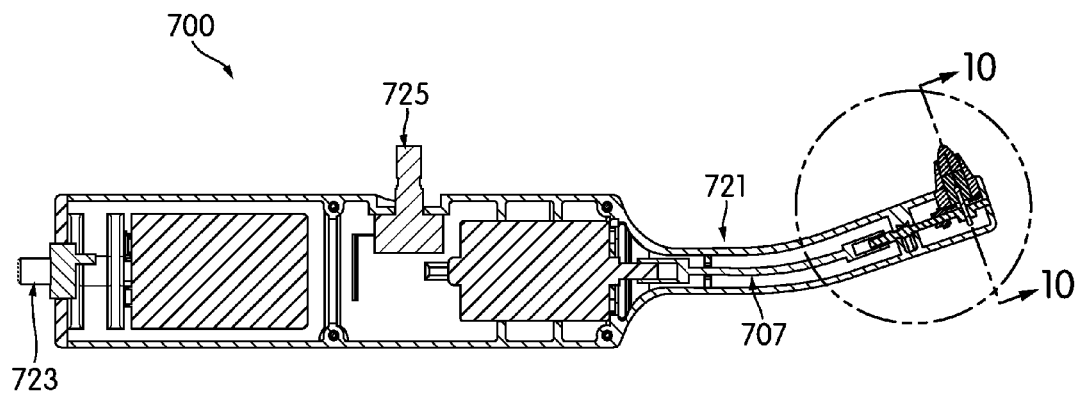
FIG. 7 is a cross-sectional view of an electric interdental cleaning apparatus in accordance with an embodiment.

FIG. 7 is a side view of an interdental cleaning device 700 in accordance with an embodiment. A drive system includes a drive member 707. The drive member 707 may be a flexible shaft, for example.

Body 701 is connected to a neck 721 at a first end of neck 721. A brush assembly is connected to a second end of neck 721. Body 701 may define an opening for access to the drive system. A first button, switch, or other now known or later developed actuating mechanism 723 may be connected to the drive system and accessible through the opening of body 701. A second button, switch, or other now known or later developed actuating mechanism 725 may be connected to the drive system and accessible through the opening of body 701. Actuating mechanism 725 may be configured to enable and cause an adjustment of the drive system. For example, actuating mechanism 725 may facilitate turning electric interdental cleaning device 700 on and off and adjusting a speed of the drive system. Drive member 721 may be flexible to accommodate angled extension from body 701 to the brush assembly. In some embodiments, the angle may be about 20 degrees.

Figure 8:
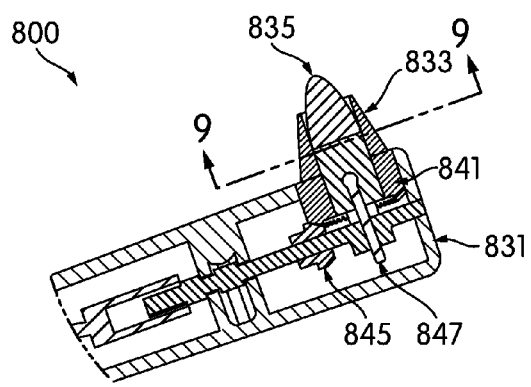
FIG. 8 is an exploded view of a brush assembly according to an embodiment.

FIG. 8 is an exploded view of a brush assembly 800, according to an embodiment of the present invention. Brush assembly 831 includes an interdental cleaning member 835 and a brush support member 833. Brush support member 833 may be configured to define a central opening and interdental cleaning member 835 may be disposed for axial and rotational movement inside the opening.

The drive member may be contained or supported within a drive shaft defined by the neck. The drive member may be connected at a second end to a crankshaft assembly having a brush assembly support gear 841 and a drive member gear 845. Drive member gear 845 may be attached to and rotated by the drive member. Drive member gear 845 may be configured to interlock with and cause rotation of brush assembly support gear 841.

The second end of the drive member may be attached to an offset connecting rod, which may be associated with a ball and socket assembly 847. The ball and socket assembly 847 may be connected to an interdental cleaning member 835, and may be configured to cause interdental cleaning member 835 to move up and down in a direction perpendicular to the direction of rotation of the drive member as the drive member rotates.

Brush support member 833 may be connected to brush assembly gear 841. When the drive member is rotated, drive member gear 845 rotates brush assembly gear 841, thus rotating interdental cleaning member 835, and in alternative embodiments, brush support member 833. Meanwhile, the rotating drive member moves the connecting rod and ball and socket assembly to cause pulsing movement of interdental cleaning member 835 through the central opening of brush support member 833. In some embodiments, interdental cleaning member 835 may also be connected to brush assembly gear 841 to enable rotation of cleaning member 835 during the pulsing. For example, when a gear ratio of brush assembly gear 841 and drive member gear 845 is 1:2, interdental cleaning member 833 may pulse in a direction perpendicular to a direction of rotation at a speed of about twice that of the speed of rotation.

Figure 9:
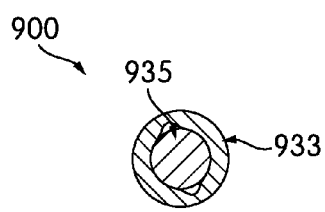
FIG. 9 is a top view of a brush assembly for an electric interdental cleaning apparatus in accordance with an embodiment.

FIG. 9 is a top view of a brush assembly 900 in accordance with an embodiment. Brush assembly 900 includes a centrally disposed interdental cleaning member 935. Interdental cleaning member 935 is configured to rotate and pulse within the opening defined by a brush support member 933. In an alternative embodiment, interdental cleaning member 935 may be configured to meet a brush support to cause rotation of interdental cleaning member 935 as brush support member 933 rotates, brush support member 933 being caused to rotate by a gear assembly. The gear assembly and brush support member 933 may be keyed to interdental cleaning member 935 to cause rotation of interdental cleaning member 935 by way of the gear assembly, and to restrict axial movement of interdental cleaning member 935.

Figure 10:
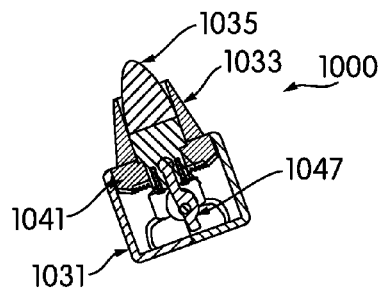
FIG. 10 is a cross-sectional end view of a head of an electric interdental cleaning apparatus in accordance with an embodiment.

FIG. 10 is a cross-sectional end view of a head 1000 of an electric interdental cleaning device 1000 in accordance with an embodiment. Head 1000 includes an interdental cleaning member 1035 and a brush support member 1033. Brush support member 1033 may be configured to define a central opening, and interdental cleaning member 1035 may be disposed for movement inside the ring in a direction substantially perpendicular to a direction of rotation.

A drive member may be contained or supported within a drive shaft defined by a neck (not shown). The drive member may be connected at a second end to a crankshaft assembly having a brush assembly support gear 1041 and a drive member gear (not shown). The drive member gear may be attached to and rotated by the drive member. The drive member gear may be configured to interlock with and cause rotation of brush assembly support gear 1041.

The drive member may be attached to an offset connecting rod. The connecting rod may be associated with a ball and socket assembly 1047. Ball and socket assembly 1047 may connected to interdental cleaning member 1035, and may be configured to cause interdental cleaning member 1035 to move up and down in a direction perpendicular to direction of rotation of the drive member as the drive member rotates.

Interdental cleaning member 1035 may be connected to brush assembly gear 1041. When the drive member is rotated, a drive member gear (not shown) rotates interdental cleaning member 1035. Meanwhile, the rotating drive member moves the connecting rod and ball and socket assembly to cause pulsing movement of interdental cleaning member 1035 through the central opening of brush support member 1033. Interdental cleaning member 1035 may be connected to brush assembly gear 1041 to enable rotation during the pulsing. For example, when a gear ratio of brush assembly gear 1041 and drive member gear 1041 is 1:2, the interdental brush may rotate, and pulse in a direction perpendicular to a direction of rotation at a speed of about twice that of the speed of rotation of interdental member 1035.

Figure 11A:
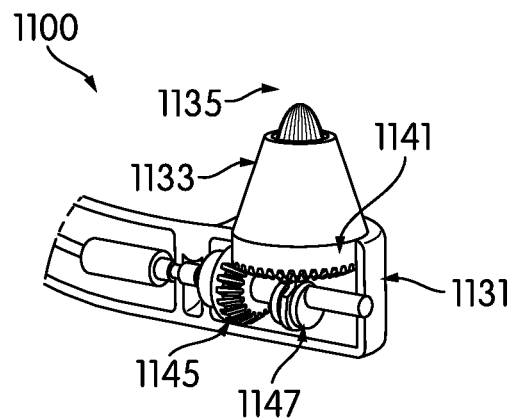
FIG. 11A is a perspective view of a head of an electric interdental cleaning apparatus in accordance with an embodiment, wherein an interdental cleaning member is in a first position.
Figure 11B:
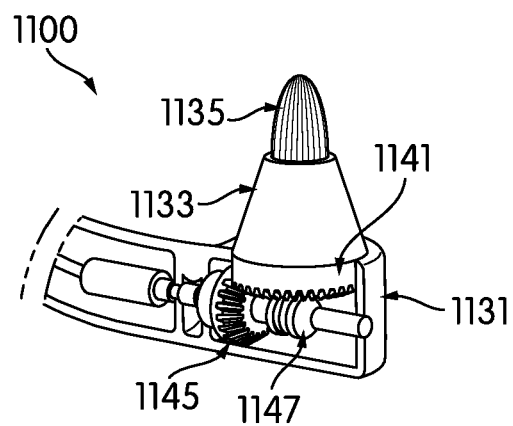
FIG. 11B is a perspective view of the head of the electric interdental cleaning apparatus of FIG. 11A, wherein the interdental cleaning member is a second position that is different than the first position.
Figure 11C:
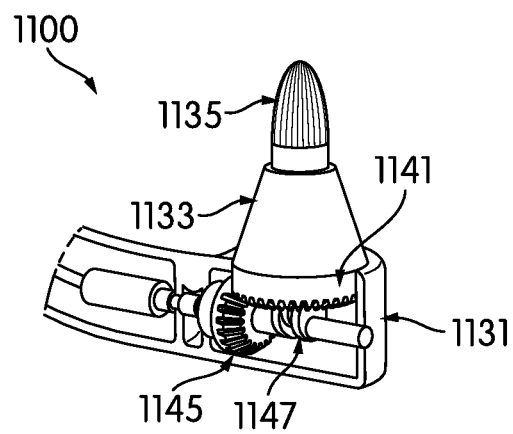
FIG. 11C is a perspective view of the head of the electric interdental cleaning apparatus of FIG. 11A, wherein the interdental cleaning member is in a third position that is different than the first position and the second position.

FIGS. 11A-C are perspective views of a head 1100 of an electric interdental cleaning device in accordance with an embodiment. Head 1100 includes an interdental cleaning member 1135 and a brush support member 1133. Brush support member 1133 may be configured to form a ring defining a central opening, and interdental cleaning member 1135 may be disposed for axial and rotational movement inside the opening.

A drive member may be connected at a second end to a crankshaft assembly having a brush assembly support gear 1141 and a drive member gear 1145. Drive member gear 1145 may be attached to and rotated by the drive member. Drive member gear 1145 may be configured to interlock with and cause rotation of brush assembly support gear 1141.

A second end of the drive member may be attached to an offset connecting rod. The connecting rod may be associated with a ball and socket assembly 1147. Ball and socket assembly 1147 may connected to interdental cleaning member 1135, and may be configured to cause interdental cleaning member 1135 to move up and down in a direction perpendicular to direction of rotation of the drive member as the drive member rotates. In FIG. 11A, interdental cleaning member 1135 is in a first, fully retracted position or non-extended position where ball and socket assembly 1147 supports interdental cleaning member 1135 in a first, least extended position. For example, in a first position the interdental member may extend about 5 mm beyond the brush support member 1133.

In FIG. 11B, interdental cleaning member 1135 is located at a second position that is about midway between the first least extended position shown in FIG. 11A and a third most extended position shown in FIG. 11C, where interdental cleaning member 1635 is substantially fully extended. For example, the interdental cleaning member 1135 may be configured to be extendible to about 1 centimeter beyond the brush support member 1133.

Accordingly, the interdental cleaning device in accordance with embodiments discussed herein advantageously enable enhanced and efficient cleaning of teeth and interdental spaces. The electric interdental cleaning device may be useful for many applications, including pedodontal, and orthodontic applications.

The interdental cleaning device may be useful for periodontal applications, and may enable enhanced cleaning under the gumline. For example, the interdental cleaning device in accordance with embodiments may include an interdental cleaning member that is configured to reach about 3 to 5 millimeters below the gumline for cleaning. Preferably, the electric interdental cleaning device is constructed to enable cleaning at about 5 millimeters below the gumline.

It will be readily understood that the components of various embodiments of the present invention, as generally described and illustrated in the figures herein, may be arranged and designed in a wide variety of different configurations. Thus, the detailed description of the embodiments of the systems, apparatus, and methods, as represented in the attached figures, is not intended to limit the scope of the invention as claimed, but is merely representative of selected embodiments.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

The modifiers "about" and "approximately" used in connection with a quantity are inclusive of the stated value and have the meaning dictated by the context. For example, it includes at least the degree of error associated with the measurement of the particular quantity. When used with a specific value, they also disclose that value.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

It would be apparent to those of skill in the art that certain modifications, variations, and alternative constructions would be apparent, while remaining within the spirit and scope of the invention. In order to determine the metes and bounds of the invention, therefore, reference should be made to the appended claims.

What is claimed is:

1. A powered, electric interdental cleaning apparatus, comprising:
   a body comprising a first end and a second end;
   an interdental cleaning member configured for cleaning interdental surfaces and spaces including a tooth surface under gum tissue,
   the interdental cleaning member comprising a brush and a brush support, the brush support defining an opening and the brush axially moveable from a first position to a second position,
   the brush contained within the brush support in the first position and extending above the opening in the second position;
   a drive member extending from the first end of the body at an angle to a longitudinal axis of the body, the drive member connected to the interdental cleaning member; and
   a neck comprising a first end and a second end, the neck extending from the first end of the body at the first end of the neck to a head comprising the interdental cleaning member, the neck defining a drive member shaft that contains the drive member.

2. The apparatus of claim 1, the cleaning member further comprising:
   a plurality of bristles.

3. The apparatus of claim 2, wherein the plurality of bristles are angled to form a point.

4. The apparatus of claim 1, wherein the brush support is fixedly attached to the head.

5. The apparatus of claim 1, wherein the brush support is configured to rotate.

6. The apparatus of claim 1, wherein the drive member comprises a flexible metal shaft.

7. The apparatus of claim 1, wherein the drive member extends from the body at an angle of about 20 degrees.

8. The apparatus of claim 1, wherein the drive member causes axial and rotational movement of the interdental cleaning member.

9. A brush assembly, comprising:
   a brush support; and
   an interdental cleaning member surrounded by the brush support, wherein
   the brush support and the interdental cleaning member are configured and
   arranged to enable the interdental cleaning member to rotate and reciprocate axially through an opening in the brush support.

10. The apparatus of claim 9, wherein the brush interdental cleaning member support is configured to extend 5 millimeters beyond an opening of the brush support at a non-extended position.

11. The apparatus of claim 10, wherein the interdental cleaning member is configured to extend about 1 centimeter beyond an opening of the brush support at a fully extended position.

12. The apparatus of claim 9, wherein the brush support is configured to rotate the interdental cleaning member.

13. The apparatus of claim 9, wherein the brush support is fixed and non-rotatable.

14. The apparatus of claim 9, wherein the interdental cleaning member comprises a central bristle tuft.

15. The apparatus of claim 9, wherein the brush is axially moveable from a first position to a second position, wherein the brush is contained within the brush support in the first position and the brush extends above the opening in the second position.

16. A powered dental and interdental cleaning apparatus, comprising:
- a brush support;
- an interdental cleaning member surrounded by the brush support, wherein the brush support and the interdental cleaning member are configured and arranged to enable the interdental cleaning member to rotate and reciprocate axially through an opening in the brush support; and
- a drive assembly configured to rotate the interdental cleaning member and cause pulsing movement of the interdental cleaning member through the opening.

17. The apparatus of claim 16, further comprising:
a body containing the drive assembly and a brush assembly, wherein the brush assembly comprises the interdental cleaning member.

18. The apparatus of claim 16, wherein the drive assembly further comprises:
a drive member extending from a first end of a body at an angle to a longitudinal axis of the body, wherein the drive member is connected to the interdental cleaning member to rotate the interdental cleaning member and cause the interdental cleaning member to move axially.

19. The apparatus of claim 18, wherein the drive member connects to the interdental cleaning member by way of a gear comprising a keyed surface configured to mate with a surface of the interdental member to cause the interdental member to rotate.

20. The apparatus of claim 16, further comprising:
a variable speed motor connected to and configured to drive the drive member, wherein the drive member extends from the body at an angle of about 20 degrees.

21. The apparatus of claim 16, wherein the brush is axially moveable from a first position to a second position, wherein the brush is contained within the brush support in the first position and the brush extends above the opening in the second position.

* * * * *